United States Patent [19]

Borken

[11] 4,277,681
[45] Jul. 7, 1981

[54] LOW RADIATION DENSITOMETER

[75] Inventor: Richard J. Borken, St. Louis Park, Minn.

[73] Assignee: Honeywell Inc., Minneapolis, Minn.

[21] Appl. No.: 81,962

[22] Filed: Oct. 4, 1979

[51] Int. Cl.³ .................... G01N 23/00; G01N 21/01
[52] U.S. Cl. ........................... 250/358 R; 250/432 R
[58] Field of Search ................ 250/308, 336, 358 R, 250/359, 360, 356, 432 R; 73/32 R

[56] References Cited

U.S. PATENT DOCUMENTS

| | | |
|---|---|---|
| 2,316,239 | 4/1943 | Hare . |
| 2,757,290 | 7/1956 | Jacobs et al. . |
| 2,763,790 | 9/1956 | Ohmart . |
| 2,898,466 | 8/1959 | Lintz et al. . |
| 2,903,590 | 9/1959 | Somerville . |
| 2,922,888 | 1/1960 | Faulkner et al. . |
| 2,968,729 | 1/1961 | Pepper et al. . |
| 3,196,271 | 7/1965 | Wright . |
| 3,452,192 | 6/1969 | Hanken . |
| 3,508,046 | 4/1970 | Anton et al. . |
| 3,697,730 | 10/1972 | Clack et al. . |
| 3,729,982 | 5/1973 | Senda . |
| 3,842,656 | 10/1974 | Battista . |
| 3,889,121 | 6/1975 | Bossen . |
| 3,903,732 | 9/1975 | Rork et al. . |
| 4,129,778 | 12/1978 | Inoue et al. . |
| 4,140,906 | 2/1979 | Morrison et al. . |

Primary Examiner—Alfred E. Smith
Assistant Examiner—Janice A. Howell
Attorney, Agent, or Firm—Charles J. Ungemach

[57] ABSTRACT

Apparatus for determining the density of fluids in containers utilizing an x-ray source and two radiation detectors located at different distances from the source by a known amount. The outputs of the detectors are ratioed to produce a signal which varies with the density of the fluid lying between the source and the two detectors.

13 Claims, 1 Drawing Figure

LOW RADIATION DENSITOMETER

BACKGROUND OF THE INVENTION

Apparatus for determining the density of materials and particularly fluids in containers are known in the prior art. Many such schemes are mechanical and require the measurement of the position or the force on a buoyant float. Other types require the determination of the resonant frequency of a piezoelectric material or the determination of the refracted index of the material. Another type which has the advantage of requiring no moving parts and low cost is a radiation type. One useful form of such apparatus is a radiation type densitometer in which a source of radiation is placed on one side of the material to be measured and a radiation detector placed on the other side. The amount of attenuation of radiation by the material is a measure of the density. Patents such as D. G. C. Hare, U.S. Pat. No. 2,316,239 issued Apr. 13, 1943, P. E. Ohmart U.S. Pat. No. 2,763,790 issued Sept. 18, 1956, M. Lintz et al U.S. Pat. No. 2,898,466 issued Aug. 4, 1959, T. P. Pepper et al U.S. Pat. No. 2,968,729 issued Jan. 17, 1961, W. H. Faulkner et al U.S. Pat. No. 2,922,888 issued Jan. 26, 1960 and D. E. Wright U.S. Pat. No. 3,196,271 issued July 20, 1965 all show one or two detector systems for measuring density. Radiation density measuring devices have encountered difficulties in the past due to several problems. One detector systems have difficulty when the radiation source decays or residue builds up on the apparatus since the detector cannot distinguish between reduction of radiation from a decaying source and increased attenuation from the material being measured. Efforts to solve this problem have resulted in two detector systems wherein a first radiation detector and radiation source are situated with respect to the unknown material and a second radiation detector and source are situated with respect to a reference material and the outputs of the two detectors are subtracted so that the decay of radiation source is eliminated from the equations. The difficulty with these type systems has been that the detector efficiencies usually vary in a way which is not compensated for by a subtracting type system. Furthermore, using a reference material or source requires additional apparatus which may be difficult to accommodate in certain situations such as in aircraft use. Some prior art systems have utilized detectors mounted on the outsides of containers in which the material to be measured is located and such systems have difficulty because of the absorption characteristics of the container itself which must be compensated for. Furthermore, use of a "standard" reference material and subtracting detector signals to compensate for errors in source decay does not compensate for the type of errors which are common to both detector measurement chains.

Radiation detector systems have also encountered difficulty with public acceptance since radiation sources have often been unsafe because of high radiation levels and extra apparatus is needed to provide shielding.

SUMMARY OF THE INVENTION

The apparatus of the present invention utilizes an x-ray source which is quite "clean" being of the type that is used in household smoke detectors. The present invention utilizes two detectors placed in the fluid whose density is to be measured along with this x-ray source. By placing the source and the detectors in the fluid, the difficulty of compensating for the container walls is avoided. The two detectors are placed in the fluid at different distances from the x-ray source so that both detectors receive radiation from the same source and thus avoid the problem of residue build-up for the sources and/or the detectors of the prior art. By placing the detectors at different distances from the source, this residue build-up will be sensed by both detectors but since the detectors receive x-rays after different amounts of attenuations, the effects of such residue build-up can be removed from the equations. The outputs of the two detectors are ratioed rather than subtracted and by ratioing these signals the problem that relates to different detector efficiencies is reduced and the problem that relates to errors common to both detector measurement chains is reduced. Thus, the device does not need recalibration as often as prior art systems.

DETAILED DESCRIPTION OF THE PREFERRED EMBODIMENTS

Figure 1:
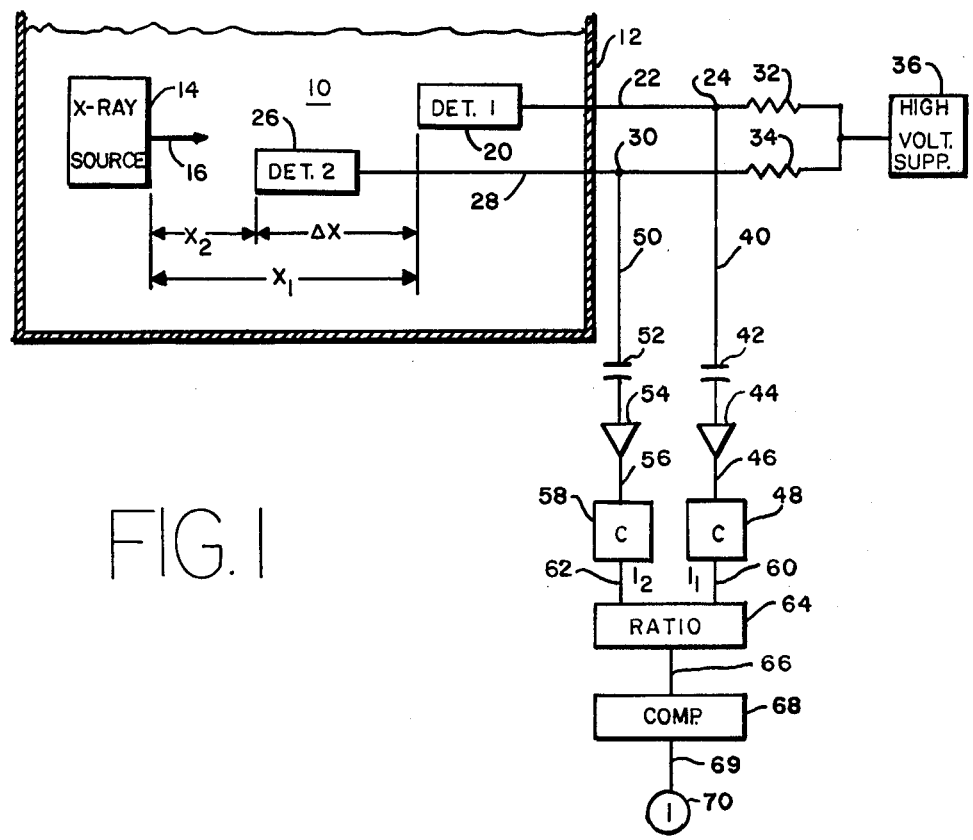
FIG. 1 shows a schematic drawing of the present invention as used for the measurement of fluid density in a container.

In FIG. 1 a fluid 10, which may be the jet fuel of an aircraft, is shown within a container 12 which may be one of the aircraft fuel tanks. An x-ray source 14 is shown mounted in the fluid within the container so as to produce radiation generally along a direction shown by arrow 16. X-ray source 14 is preferrably an americium-241 x-ray source. The 60 keV x-ray energy which is characteristic of americium-241 is preferrable to x-ray energies which are characteristic of other radioactive isotopes for fluid density measurement. This is because the attenuation properties of jet fuel, utilizing 60 keV x-rays, are such that reasonable geometries, for example, can be used and because the inherent density error due to the presence in the fuel of jet fuel contaminants, principally sulfur, is kept to an acceptable minimum. Also, the americium-241 source can be configured so as to effectively emit monoenergetic 60 keV x-rays and it has adequate yield and a long half-life. The technology with regard to manufacturing safe, reliable, and inexpensive americium-241 sources is well advanced. Americium-241 emits no high-energy, gamma radiation nor any other form of high-energy radiation, thus a device incorporating this source can easily be built so that there is substantially no radiation external to the device. By using this source, no x-ray generation apparatus is needed.

A first radiation detector 20, identified as DET. 1, is mounted in the fluid 10 of container 12 at a distance $x_1$ from the x-ray source 14 and also in the general direction of the arrow 16 therefrom. Detector 20 operates to detect radiation eminating from source 14 so as to produce charge pulse signals at a rate indicative of the radiation received which signals are presented on a line 22 which passes through container 12 to a junction point 24. A second radiation detector 26, identified as DET. 2, is shown in the fluid 10 within container 12 mounted at a distance $X_2$ from x-ray source 14 and also in the general direction of the arrow 16 therefrom. Detector 26 also operates to produce charge pulse signals at a rate indicative of the radiation received which signals are presented on a line 28 passing through the wall of container 12 to a junction point 30. Detectors 20 and 26 ae preferrably of the proportional counter type but might be of other common types known in the art. Junction points 24 and 30 are connected by a pair of resistors 32 and 34 to a high voltage supply 36 which operates to provide excitation for the detectors 20 and 26. Resistors 32 and 34 serve to isolate the output signals of the two detectors from one another. Junction joint 24 is connected by a conductor 40 to one side of a capacitor 42, the other side of which is connected to a charge amplifier circuit 44. The output of amplifier circuit 44 is connected by a conductor 46 to a pulse counter 48. Junction point 30 is connected by a conductor 50 to one side of a capacitor 52, the other side of which is connected to a charge amplifier circuit 54. Capacitors 42 and 52 are blocking capacitors to isolate the amplifiers 44 and 54 from the high voltage on lines 22 and 28. The output of amplifier circuit 54 is connected by a conductor 56 to a second pulse counter 58. The output of counter 48, identified as $I_1$, appears on a conductor 60 while the output of counter 58, identified as $I_2$, appears on a conductor 62. Conductors 60 and 62 are connected to the inputs of a ratioing device 64 having an output on a conductor 66 indicative of the ratio $I_1/I_2$ which output is presented to a computer shown as box 68 which takes the $I_1/I_2$ signal on line 66 and, after a period of time, determined as a clock signal which is not shown but which may be internal to computer 68, computes the density from the equation (7) below. This density is presented on a line 69 to an indicator 70, or, alternatively, to a fuel gauge system which will utilize the density signal along with a signal indicative of fuel volume obtained elsewhere to provide the pilot with a fuel mass indication.

In operation, detectors 20 and 26 receive radiation from source 14 in amounts which depend upon the strength of the source 14, the distance of the detectors from the source, the amount of residue build-up and upon the attenuation characteristics of the fluid 10 which is a function of its density. The signals which appear at points 24 and 30 will therefore be a function of these variables and the detection efficiency of detectors 20 and 26. These signals are fed through capacitors 42 and 52 to amplifier circuits 44 and 54, which circuits, in addition to amplifying, may also contain threshold circuits to eliminate background noise. Counters 48 and 58 operate on the amplified signals to produce count signals $I_1$ and $I_2$ whose magnitude varies with the amount of radiation received by detectors 20 and 26. $I_1$ can be expressed by the equation:

$$I_1 = I_{01} B \exp(-KX_1) \quad (1)$$

where $I_1$ is the measured count on line 60, $I_{01}$ is a value indicative of the count rate which would be received by detector 20 if there were no material 10 in the path, B is a transmission factor related to residue build-up, K is the linear attenuation coefficient and $X_1$ is the distance between the source 14 and detector 20 in FIG. 1. $I_2$ can be expressed by the equation:

$$I_2 = I_{02} B \exp(-KX_2) \quad (2)$$

where $I_2$ is the measured count rate appearing on line 62, $I_{02}$ is a value indicative of the count rate which would be received by detector 26 if there were no material 10 in the path and $X_2$ is the distance between source 14 and detector 26 in FIG. 1.

The linear attenuation coefficient K is related to the density of the fluid 10 in FIG. 1 by the equation:

$$K = \mu \rho \quad (3)$$

where $\mu$ is the mass attenuation coefficient and $\rho$ is the density of the fluid 10.

Taking the ratio of equations (1) and (2), the following equation results:

$$\frac{I_1}{I_2} = \frac{I_{01} B \exp(-KX_1)}{I_{02} B \exp(-KX_2)} = \frac{I_{01}}{I_{02}} \exp(-K\Delta X) \quad (4)$$

where $\Delta X$ is the difference between the distance detector 20 is spaced from source 14 and the distance detector 26 is spaced from source 14; i.e., $X_1-X_2$. It should be noted that the transmission factor B relating to residue build-up was cancelled out of the equation. It has also been found that while the efficiencies of the detectors may change, due for example to changes of environmental conditions or changes in the operating point of the high voltage source, such changes are proportional when proportional type detectors are employed so that by ratioing the signals, any changes in detector efficiencies, which are inherent in $I_{01}$ and $I_{02}$, allow the ratio $I_{01}/I_{02}$ to be constant. Equation (4) may be rewritten as follows:

$$\log_e\left(\frac{I_1}{I_2}\right) = -K\Delta X + \log_e\left(\frac{I_{01}}{I_{02}}\right) \quad (5)$$

Substituting equation (3) into equation (5) produces the result:

$$\log_e\left(\frac{I_1}{I_2}\right) = -\mu\rho\Delta X + \log_e\left(\frac{I_{01}}{I_{02}}\right) \quad (6)$$

which may be rewritten as:

$$\rho = \frac{-1}{\mu\Delta X} \log_e\left(\frac{I_1}{I_2}\right) + \frac{1}{\mu\Delta X} \log_e\left(\frac{I_{01}}{I_{02}}\right) \quad (7)$$

As can be seen by equation (7), the density of the fluid 10 may be determined by measuring the ratio $I_1/I_2$ since $\Delta X$ is a fixed quantity and $\log_e I_{01}/I_{02}$ is constant and $\mu$, although somewhat changeable due to varying trace amounts of sulfur that may exist in jet fuel, does not vary enough to change the density measurement by more than about ±0.2% depending on the sulfur content which is set to within certain predetermined limits by specifications.

In FIG. 1, ratioing device 64 takes the ratio of $I_1/I_2$ so that the signal appearing on line 66 is proportional thereto and computer 68 operates on the $I_1/I_2$ value to derive the output signal on line 69 indicative of $\rho$ from equation (7). This output signal causes indicator 70 or the aircraft fuel measurement system to receive an indication of the density desired.

Accordingly, it is seen that I have provided densitometer apparatus which overcomes the problems of the prior art and produces a simple, safe, low cost and accurate measure of density and which compensates for source decay and residue build up which may occur on the source or detectors over a period of time. Many changes and modifications to this apparatus disclosed in connection with the preferred embodiment will occur to those skilled in the art and I do not wish to be limited to the disclosures used therewith. I intend only to be limited by the following claims.

The embodiments of the invention in which an exclusive property or right is claimed are defined as follows:

1. Apparatus for measuring fluid density comprising, in combination:
    a source of radiation operable to emit radiation generally along a first path;
    first and second radiation detectors each operable to produce an output signal indicative of the radiation received thereby;
    means mounting the source and the radiation detectors in the fluid whose density is to be measured with the first detector in the first path at a first distance from the source and the second detector in the first path at a second distance from the source; and
    ratio means connected to the radiation detectors to receive the output signals therefrom and to produce a ratio signal which varies with the density of the fluid.

2. Apparatus according to claim 1 further including computing means connected to the ratio means to receive the ratio signal and operable to produce a resultant signal indicative of the density of the fluid.

3. Apparatus according to claim 2 further including indicator means connected to the computing means to receive the resultant signal.

4. Apparatus according to claim 1 wherein the source is an americium-241 -x-ray source.

5. Apparatus according to claim 1 wherein the radiation detectors are proportional counters.

6. Apparatus according to claim 2 wherein the output signal of the first and second detectors are $I_1$ and $I_2$ respectively and are expressed by the equations $$I_1 = I_{01} B \exp(-KX_1) \text{ and}$$

$$I_2 = I_{02} B \exp(-KX_2)$$

respective where $I_{01}$ and $I_{02}$ are values indicative of the values $I_1$ and $I_2$ would have if there were no fluid between the source and the first and second radiation detectors, B is a value related to residue build up on the source and on the first and second radiation detectors, K is the linear attenuation coefficient which varies with the density of the fluid, $X_1$ is the first distance, and $X_2$ is the second distance and wherein the ratio signal is expressed by the equation $$\frac{I_1}{I_2} = \frac{I_{01}}{I_{02}} \exp(-K\Delta X)$$

where $\Delta X$ is the difference between the first and second distances.

7. Apparatus according to claim 6 wherein the resultant signal is expressed by the equation $$\rho = \frac{-1}{\mu \Delta X} \log_e \left(\frac{I_1}{I_2}\right) + \frac{1}{\mu \Delta X} \log_e \left(\frac{I_{01}}{I_{02}}\right)$$

where $\rho$ is the density of the fluid and $\mu$ is the mass attenuation coefficient of the fluid.

8. Apparatus of the class described comprising, in combination:
    a source of radiation operable to emit radiation generally through a material along a first path;
    a first radiation detector mounted in the first path at a distance $X_1$ from the source and operable to produce an output signal $I_1$ indicative of the radiation received thereby;
    a second radiation detector mounted in the first path at a distance $X_2$ from the source and operable to produce an output signal $I_2$ indicative of the radiation received thereby; and
    signal receiving means connected to the first and second radiation detectors to receive $I_1$ and $I_2$ and to produce a ratio signal which varies with $I_1/I_2$ and thus with the density of the material.

9. Apparatus according to claim 8 wherein the first and second radiation detectors are of the proportional type.

10. Apparatus according to claim 9 wherein $I_1 = I_{01} B \exp(-KX_1)$, $I_2 = I_{02} B \exp(-KX_1)$ where K is the linear attenuation coefficient of the material which is equal to the density of the material times the mass attenuation coefficient of the material, B is a value related to the residue build up on the source and the first and second radiation detectors, and $I_{01}$ and $I_{02}$ are values indicative of the values $I_1$ and $I_2$ would have if there were no material between the source and the first and second radiation detectors.

11. Apparatus according to claim 10 further including computing means connected to the signal receiving means to receive the ratio signal and operable to produce a resultant signal indicative of the density of the material according to the equation $$\rho = \frac{-1}{\mu \Delta X} \log_e \left(\frac{I_1}{I_2}\right) + \frac{1}{\mu \Delta X} \log_e \left(\frac{I_{01}}{I_{02}}\right)$$

where $\rho$ is the density of the material, $\mu$ is the mass attenuation coefficient of the material and $\Delta X = X_1 - X_2$.

12. Apparatus according to claim 11 further including an indicator connected to the signal receiving means to receive the resultant signal.

13. Apparatus according to claim 12 wherein the source is an americium-241 x-ray source.

* * * * *